US00PP22256P2

(12) United States Plant Patent
Heuger

(10) Patent No.: US PP22,256 P2
(45) Date of Patent: Nov. 15, 2011

(54) ***HELLEBORUS* PLANT NAMED 'COSEH 770'**

(50) Latin Name: *Helleborus×nigercors*
Varietal Denomination: COSEH 770

(76) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 12/799,439

(22) Filed: Apr. 23, 2010

(51) Int. Cl.
*A01H 5/00* (2006.01)

(52) U.S. Cl. ..... Plt./439
(58) Field of Classification Search ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'COSEH 770', characterized by its upright and mounding plant habit; uniform and freely flowering habit; dark green-colored leaves; long flowering period; single light green-colored flowers; and good garden performance.

2 Drawing Sheets

Botanical designation: *Helleborus×nigercors*.
Cultivar denomination: 'COSEH 770'.

BACKGROUND OF THE INVENTION

The present invention relates to a new and distinct cultivar of *Helleborus* plant, botanically known as *Helleborus×nigercors*, and hereinafter referred to by the name 'COSEH 770'.

The new *Helleborus* plant is a product of a planned breeding program in Glandorf, Germany. The objective of the breeding program was to create new uniform *Helleborus* plants with unique and attractive leaf and flower coloration and resistance to pests.

The new *Helleborus* plant originated from a cross-pollination conducted by the Inventor in Glandorf, Germany in November, 2002 of two unnamed proprietary seedling selections of *Helleborus×nigercors*, not patented. The new *Helleborus* plant was discovered and selected by the Inventor as a single flowering plant from within the progeny of the stated cross-pollination grown in a controlled greenhouse environment in Glandorf, Germany in February, 2005.

Asexual reproduction of the new *Helleborus* plant by divisions in a controlled greenhouse environment in Glandorf, Germany since March, 2005, has shown that the unique features of this new *Helleborus* plant are stable and reproduced true to type in successive generations.

SUMMARY OF THE INVENTION

Plants of the new *Helleborus* have not been observed under all possible environmental conditions. The phenotype may vary somewhat with variations in cultural practices and environmental conditions such as temperature and light intensity without, however, any variance in genotype.

The following traits have been repeatedly observed and are determined to be the unique characteristics of the *Helleborus* 'COSEH 770'. These characteristics in combination distinguish the *Helleborus* 'COSEH 770' as a new and distinct *Helleborus* plant:

1. Upright and mounding plant habit.
2. Uniform and freely flowering habit.
3. Dark green-colored leaves.
4. Long flowering period.

5. Single light green-colored flowers.
6. Good garden performance.

Compared to plants of the parent selections, plants of the new *Helleborus* flower more freely and more uniformly.

Plants of the new *Helleborus* can be compared to plants of *Helleborus niger×Helleborus lividus* 'COSEH 700', disclosed in U.S. Plant Pat. No. 21,003. Plants of the new *Helleborus* differ primarily from plants of 'COSEH 700' in the following characteristics:

1. Plants of the new *Helleborus* have lighter green-colored leaves than plants of 'COSEH 700'.
2. Plants of the new *Helleborus* and 'COSEH 700' differ in flower color.

BRIEF DESCRIPTION OF THE PHOTOGRAPHS

The accompanying colored photographs illustrate the overall appearance of the new *Helleborus* plant and show the colors as true as it is reasonably possible to obtain in colored reproductions of this type.

Colors in the photographs may differ slightly from the color values cited in the detailed botanical description which accurately describe the colors of the new *Helleborus* plant.

The photograph on the first sheet comprises a side perspective view of a typical flowering plant of 'COSEH 770' grown in a container.

The photograph on the second sheet is a close-up view of a typical flower of 'COSEH 770'.

DETAILED BOTANICAL DESCRIPTION

The aforementioned photographs and following observations, measurements and values describe plants grown during the winter in two-liter containers in a glass-covered greenhouse in Glandorf, Germany and under conditions which closely approximate commercial *Helleborus* production. During the production of the plants, day temperatures ranged from 12° C. to 32° C. and night temperatures ranged from 3° C. to 18° C. Plants were one year old when the photographs and the description were taken. In the following description, color references are made to The Royal Horticultural Society Colour Chart, 2007 Edition, except where general terms of ordinary dictionary significance are used.

Botanical classification: *Helleborus×nigercors* 'COSEH 770'.

Parentage:

*Female, or seed, parent.*—Unnamed proprietary seedling selection of *Helleborus×nigercors*, not patented.

*Male, or pollen, parent.*—Unnamed proprietary seedling selection of *Helleborus×nigercors*, not patented.

Propagation:

*Type.*—By tissue culture.

*Time to initiate roots.*—About two months at 12° C.

*Time to produce a rooted young plant.*—About six months at 4° C. to 15° C.

*Root description.*—Thick to thin, fleshy; white to brown in color.

*Rooting habit.*—Sparse.

Plant description:

*Plant form and growth habit.*—Herbaceous perennial; upright and mounding plant habit with flowers held above the foliar plane; shape, globular; moderately vigorous growth habit.

*Plant height.*—About 31.7 cm.

*Plant diameter* (*area of spread*).—About 55.1 cm.

Foliage description:

*Arrangement.*—Leaves arranged in a basal rosette; leaves palmately compound with five leaflets per leaf.

*Leaf length.*—About 19.6 cm.

*Leaf width.*—About 19.6 cm.

*Leaflet length.*—About 12.1 cm.

*Leaflet width.*—About 5 cm.

*Leaf shape.*—Palmate; orbicular in outline.

*Leaflet shape.*—Elliptic to ovate; lower leaves occasionally cleft.

*Leaflet apex.*—Acute.

*Leaflet base.*—Attenuate.

*Leaflet margin.*—Sharply senate.

*Leaflet texture, upper and lower surfaces.*—Smooth, glabrous; leathery.

*Leaflet venation pattern.*—Pinnate.

*Leaflet color.*—Developing leaves, upper surface: Close to 137A. Developing leaves, lower surface: Close to 146A to 146B. Fully developed leaves, upper surface: Between N137A and 147A and towards the base, close to 166A, venation, close to 144A. Fully developed leaves, lower surface: Between 137D and 147B; venation, between 144C and 145A.

*Petiole.*—Length: About 14.2 cm. Diameter: About 6 mm. Texture, upper and lower surfaces: Smooth, glabrous. Color, upper and lower surfaces: Between 143B and 144A and base, close to 177B to 177C.

Flower description:

*Flower shape and habit.*—Single rotate flowers arranged on terminal cymes; freely and uniform flowering habit with about 100 flowers and flower buds per plant; flowers facing outwardly to slightly nodding and slightly upright.

*Fragrance.*—None detected.

*Natural flowering season.*—Long flowering period; plants flower from late winter to early spring in Germany.

*Flower longevity on the plant.*—About ten days; flowers not persistent.

*Flower buds.*—Length: About 1.9 cm. Diameter: About 1.3 cm. Shape: Ovate. Color: Close to 145C.

*Inflorescence height.*—About 22.5 cm.

*Inflorescence diameter.*—About 31.5 cm.

*Flower diameter.*—About 7.6 cm.

*Flower depth* (*height*).—About 2.7 cm.

*Petals.*—Transformed into nectaries.

*Sepals.*—Arrangement: About five in a single whorl. Length: About 3.8 cm. Width: About 2.8 cm. Shape: Broadly elliptic to broadly obovate. Apex: Rounded. Margin: Entire. Texture, upper and lower surfaces: Smooth, glabrous. Color: When opening, upper surface: Close to 145C, towards the base, close to 145A to 145B and towards the apex, close to 145D. When opening, lower surface: Close to 145B, towards the base, close to 145A and towards the apex, close to 145C. Fully opened, upper surface: Close to 150D and towards the base, close to 145A; with development, color becoming closer to 146B to 146C. Fully opened, lower surface: Between 145C and 150D and towards the base, close to 145A.

*Peduncles.*—Strength: Moderately strong. Length: About 9.2 cm. Diameter: About 7 mm. Aspect: About 15° from vertical. Texture: Smooth, glabrous. Color: Close to 144C.

*Pedicels.*—Strength: Moderately strong. Length: About 2.5 cm. Diameter: About 2.5 mm. Aspect: About 20° from the peduncle axis. Texture: Smooth, glabrous. Color: Close to 144C.

*Reproductive organs.*—Stamens: Quantity per flower: About 70. Filament length: About 1.4 cm. Filament color: Close to 157D. Anther shape: Narrowly reniform. Anther length: About 2 mm. Anther color: Close to 150B. Pollen amount: Moderate. Pollen color: Close to 158D. Pistils: Quantity per flower: About five. Pistil length: About 1.25 cm. Stigma shape: Club-shaped. Stigma color: Close to 150C to 150D. Style length: About 1.2 cm. Style color: Close to 150C. Ovary color: Close to 145A. Nectaries (transformed petals): Quantity per flower: About 15. Length: About 8 mm. Diameter, apex: Close to 2 mm. Diameter, base: Close to 1 mm. Shape: Flattened triangular. Color: Close to 145A and towards the apex, close to 150B.

*Seeds/fruits.*—Seed and fruit development have not been observed.

Garden performance: Plants of the new *Helleborus* have been observed to have good garden performance and to tolerate rain, wind and temperatures ranging from about −10° C. to about 35° C.

Pathogen/pest resistance: Plants of the new *Helleborus* have not been shown to be resistant to pathogens and pests common to *Helleborus*.

It is claimed:

1. A new and distinct *Helleborus* plant named 'COSEH 770' as illustrated and described.

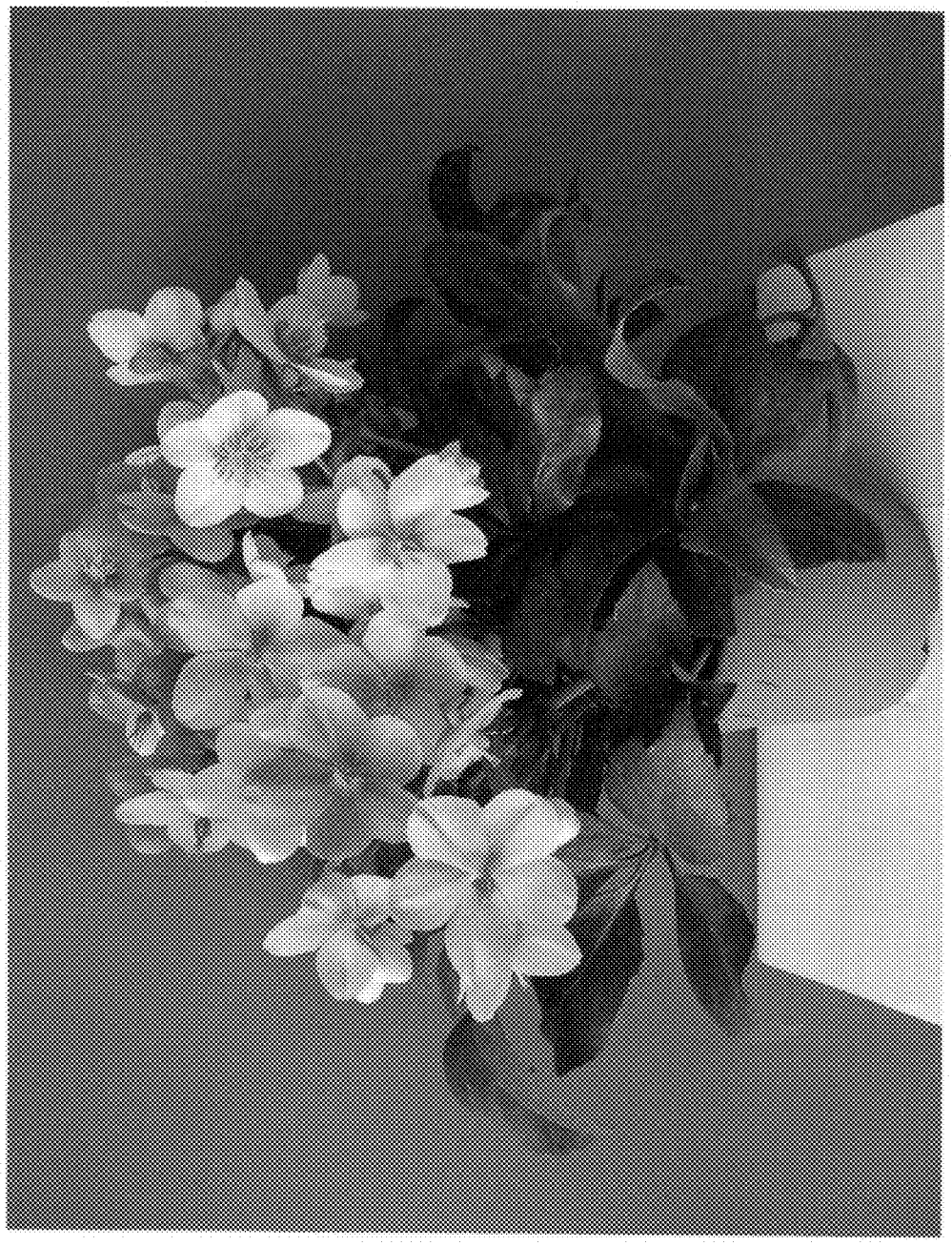

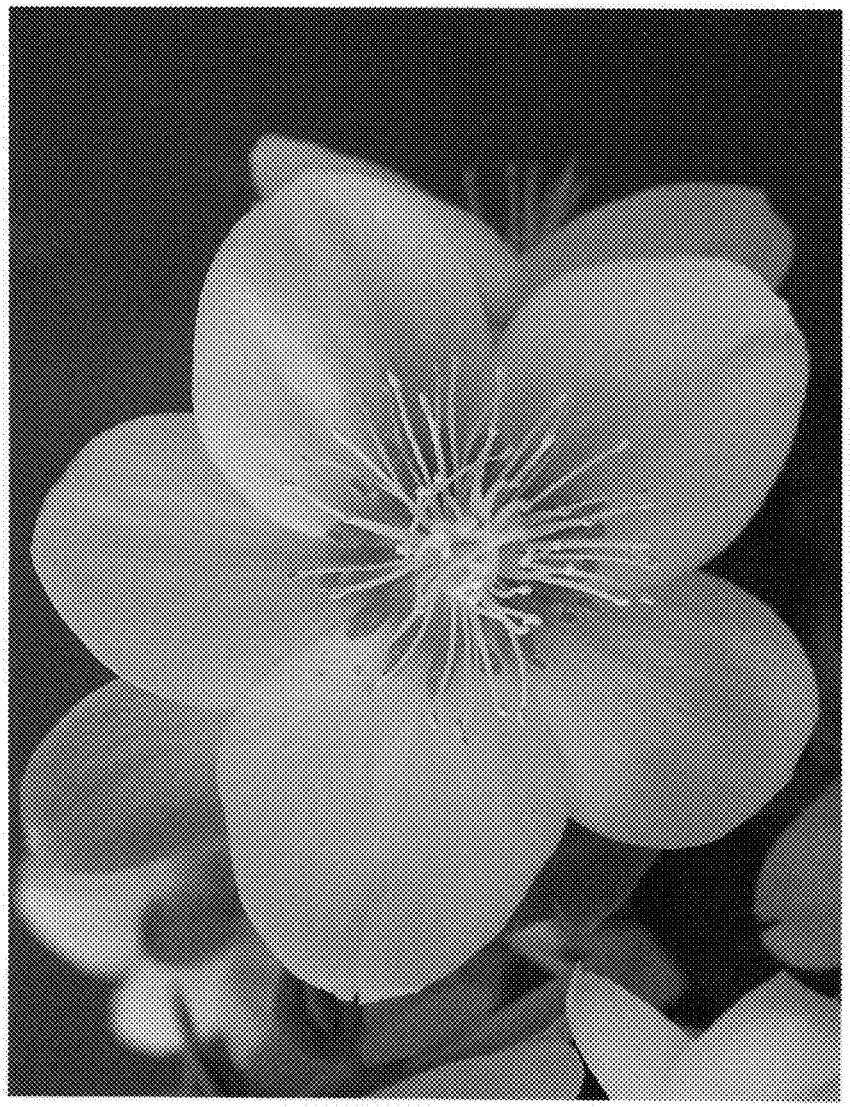

* * * * *